United States Patent [19]

Wirt

[11] Patent Number: 4,461,735
[45] Date of Patent: Jul. 24, 1984

[54] HUMIDIFIER WITH WATER OVERFLOW RELIEF MECHANISM

[75] Inventor: David F. Wirt, Oak Grove Heights Township, Pierce County, Wis.

[73] Assignee: Minnesota Mining and Manufacturing Company, Saint Paul, Minn.

[21] Appl. No.: 403,712

[22] Filed: Jul. 30, 1982

[51] Int. Cl.³ .................... B01F 3/04; A61M 15/00
[52] U.S. Cl. .................... 261/104; 128/204.13;
  137/409; 219/274; 219/275; 261/70; 261/142;
  261/154; 261/DIG. 65
[58] Field of Search ............ 261/70, 104, 107, 131,
  261/142, 153, 154, DIG. 65, DIG. 46;
  128/204.13; 137/409; 219/271–276, 362

[56] References Cited

U.S. PATENT DOCUMENTS

| | | | |
|---|---|---|---|
| 45,437 | 12/1864 | Richards | 261/70 X |
| 2,998,056 | 8/1961 | Capehart | 261/70 X |
| 3,162,235 | 12/1964 | Capehart | 261/70 X |
| 3,178,159 | 4/1965 | Johnson | 261/70 X |
| 4,192,832 | 3/1980 | Goettl | 261/70 X |
| 4,225,542 | 9/1980 | Wall et al. | 261/142 |

FOREIGN PATENT DOCUMENTS 649871 5/1979 U.S.S.R. .................. 261/70

Primary Examiner—Richard L. Chiesa
Attorney, Agent, or Firm—Donald M. Sell; James A. Smith; William L. Huebsch

[57] ABSTRACT

An evaporative humidifier having a float operated relief mechanism that is normally air tight, and will release excess water from the humidifier, should the water inlet valve malfunction, to preclude liquid water from getting into the stream of air being humidified.

5 Claims, 3 Drawing Figures 4,461,735

HUMIDIFIER WITH WATER OVERFLOW RELIEF MECHANISM

TECHNICAL FIELD

This invention relates to humidifiers of the type used to humidify air passing through ventilation devices.

BACKGROUND ART

Humidifiers are known for humidifying air passing through ventilating devices. One such humidifier which is particularly effective is that described in U.S. Pat. No. 4,225,542, the content whereof is incorporated herein by reference. Generally that humidifier comprises means for defining a main reservoir adapted for containing water, a water supply tube adapted to be coupled to a source of water under pressure for conducting water to the main reservoir, inlet float means for allowing flow of water through the supply tube when water in the main reservoir is below a first predetermined level and for normally stopping flow through the supply tube when water in the main reservoir reaches the first predetermined level; a wick having a bottom end portion projecting into the main reservoir and an opposite end portion projecting from the main reservoir; and means for directing a flow of air under greater than atmospheric pressure over the wick so that water vapor evaporating from the wick will humidify the air.

While such humidifiers normally function well, the spectre remains that if the inlet float means in such a humidifier malfunctions for any reason (e.g., such as improper assembly of the humidifier or damage to its parts caused by handling), water could rise above the first predetermined level, flood the humidifier, enter the air flow through the humidifier in its liquid state, and be carried into the breathing passageways of a patient (often an infant) connected to a ventilator in which the humidifier is used.

DISCLOSURE OF THE INVENTION

The present invention provides a relief system in a humidifier of the type described above that, in the event the inlet float means malfunctions so that it does not stop the flow of water into the humidifier when the water reaches the first predetermined level, will allow the excess water to escape from the humidifier before it rises to a level at which it can become entrained in its liquid state in the air flow through the humidifier.

According to the present invention there is provided a humidifier of the type generally described above which further includes means for defining an overflow reservoir comprising a housing having an outlet opening in a bottom portion of the overflow reservoir, outlet float means for sealing the outlet opening when water in the overflow reservoir is below a second predetermined level and for opening the outlet opening when water in the overflow reservoir rises above the second predetermined level, and an overflow tube having an inlet end within the main reservoir above the first and second predetermined levels and an outlet end in the overflow reservoir. With this structure, should water in the main reservoir rise above the first predetermined level, it will be conducted by the overflow tube to the overflow reservoir and upon reaching the second predetermined level in the overflow reservoir, will open the outlet float means and escape through the outlet opening to preclude flooding of the humidifier.

In a preferred embodiment of the present invention, the float means comprises a relief float substantially filling the overflow reservoir so that the compressible volume of the humidifier is minimized (which is desirable to facilitate the operation of the ventilator). Also, preferably the relief float is pivoted at one edge to the housing, and the outlet opening is between that one edge and the center of gravity of the relief float so that a force in excess of the weight of the relief float will be applied to seal shut the outlet opening when no water is present in the overflow reservoir.

BRIEF DESCRIPTION OF DRAWING

The present invention will further be described with reference to the accompanying drawing wherein like reference numerals refer to like parts in the several views, and wherein.

DETAILED DESCRIPTION

Figure 1:
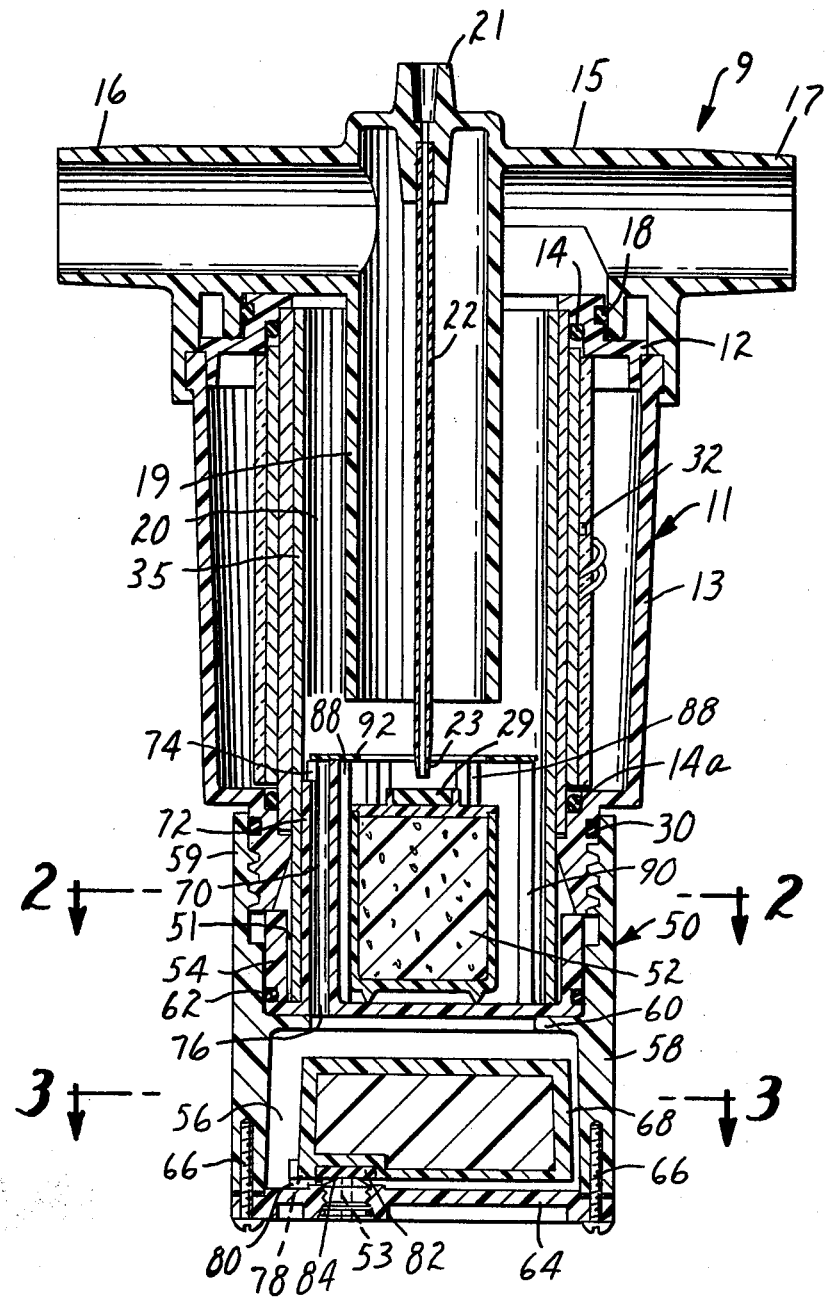
FIG. 1 is a vertical sectional view of an improved evaporative humidifier according to the present invention.
Figure 2:
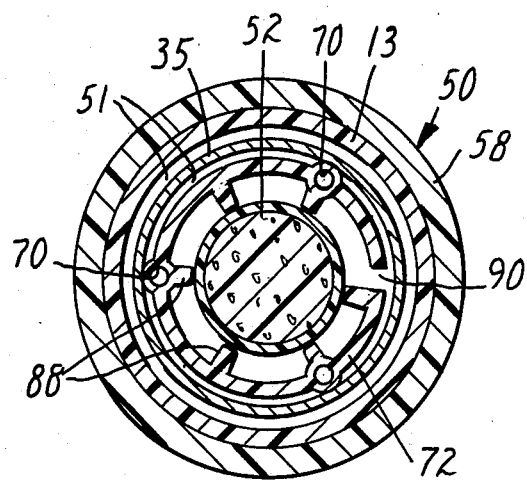
FIG. 2 is a sectional view taken approximately along line 2—2 of FIG. 1.
Figure 3:
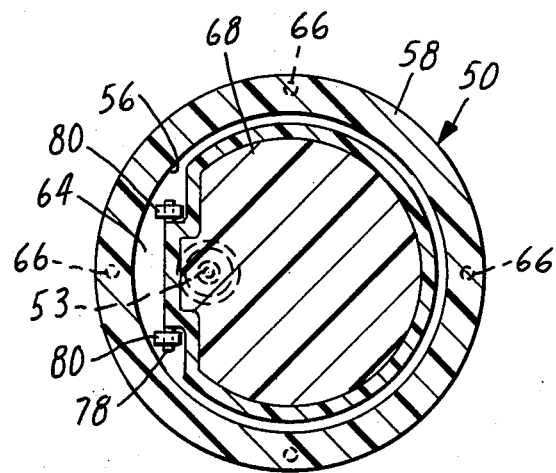
FIG. 3 is a sectional view taken approximately along line 3—3 of FIG. 1.

Referring now to the drawing, there is illustrated an improved evaporative humidifier according to the present invention, generally designated by the reference numeral 9.

The humidifier 9 normally functions in the same manner as the humidifier described in U.S. Pat. No. 4,225,542 (the disclosure whereof is incorporated herein by reference), and includes a housing 11 that comprises an air flow cap assembly 15, an annular top section 12, a generally cylindrical body member 13, and several O-ring seals 14, 14a, 18 and 30 that have essentially the same structure and function as those correspondingly named and numbered parts in the humidifier described in U.S. Pat. No. 4,225,542. Unlike that humidifier, however, the present invention has a novel bottom cap assembly 50 that replaces the bottom cap assembly of that prior humidifier, provides a main water reservoir 51 for the humidifier 9, supports a water inlet float 52 of generally the same structure and having the same function of controlling the water level in the main water reservoir 51 as did the float assembly in that prior humidifier, and incorporates a structure according to the present invention that provides a relief mechanism that will allow water to escape from the humidifier 9 through an outlet opening 53 should the water level in the main reservoir 51 exceed a predetermined level.

Normally, as described in U.S. Pat. No. 4,225,542, air in a ventilator being supplied to a patient in which ventilator the humidifier is coupled is first caused to flow into a horizontal tubular air inflow connector 16, downwardly through a vertically oriented airflow directing tube 19 and then upwardly through a central humidity chamber 20 having an outer wall defined by a cylindrical vertically oriented evaporative element or wick 35 of a water absorbing material. The lower end of the wick 35 is immersed in water contained in the main water reservoir 51 which is defined by a shallow cup-like wall 54 included in the bottom cap assembly 50. The wick 35 will draw water from the main reservoir 51 and water thus drawn up into the wick 35 is heated via a heating element 32 around the periphery of the wick 35 so that it is caused to evaporate and enter air flowing through the chamber 20. The humidified air then passes out of the chamber 20 through a tubular air outflow connector 17 into portions of a patient circuit in the ventilator which leads to a patient (not shown).

Water is supplied to the main reservoir via a water supply tube 22 connected to an external source of water under pressure (not shown) via a water inlet connector 21. Inlet float means are provided for allowing flow of water through the tube 22 when water in the main reservoir is below a first predetermined level, and for normally stopping flow through the supply tube 22 when water in the main reservoir reaches that first predetermined level. As in the humidifier described in U.S. Pat. No. 4,225,542, these means comprise the water inlet float 52 which will be separated from an outlet end 23 of the supply tube 22 to let water into the main reservoir 51 when the water level in the main reservoir 51 is below the predetermined level, but will be buoyed upwardly as water enters the main reservoir 51 until, at the predetermined water level, a soft conformable valve seat 29 is biased against the outlet end 23 of the supply tube 22 to preclude further flow of water until the water level in the main reservoir 51 drops due to absorption into and evaporation from the wick 35.

The water relief mechanism according to the present invention for allowing water to escape from the humidifier 9 through the outlet opening 53 should the water level in the main reservoir 51 exceed a predetermined level comprises an overflow reservoir 56 defined by means comprising the lower portion of a hollow cylindrical outer wall 58 included in the bottom cap assembly 50. The cylindrical outer wall 58 has an upper portion 59 that threadably engages the bottom end of the body member 13 with the O-ring 14a sealing therebetween, and has a centrally located inwardly projecting ledge 60 defining the upper limit of the overflow reservoir 54 on which ledge 60 the shallow cup-like wall 54 is supported with an O-ring seal 62 between the walls 58 and 54 to prevent water movement therebetween from the main reservoir 51. The overflow reservoir 56 is further defined by a bottom wall 64 of the bottom cap assembly 50 in which the outlet opening 53 is formed, which outlet opening 53 communicates between the overflow reservoir 54 and the atmosphere. The bottom wall 64, as illustrated, is attached to the bottom of the outer wall 58 by several screws 66 but alternatively could be attached by other means such as sonic welding. Also included is a relief float means comprising a relief float 68 for sealing the outlet opening 53 against the escape of water or gas when the water in the overflow reservoir 56 is below a second predetermined level, and for opening the outlet opening 53 when water in the overflow reservoir 56 rises above the second predetermined level. A plurality of overflow tubes 70 are formed in the peripheral wall of a hollow cylindrical upwardly projecting structure 72 which has its bottom end fixed at the center of the cup-like wall 54. Each of the tubes 70 has an upper inlet end 74 within the humidifying chamber 20 above the first predetermined level for water in the main reservoir 51 and above the second predetermined level for water in the overflow reservoir 56, and an outlet end 76 opening through the bottom of the cup-like wall 54. Thus, should water in the main reservoir 51 rise above the first predetermined level to the inlet ends 74 of the overflow tubes 70 due to some malfunction of the inlet float means, it will then flow through the overflow tubes 70 into the overflow reservoir 56 rather than rising higher in the humidifying chamber 20. The water level will then rise in the overflow chamber 56. When the water level in the overflow chamber 56 exceeds the second predetermined level, it will buoy up the relief float 68, and opening the outlet opening 53 so that the water escapes to the atmosphere through the outlet opening 53. Thus, water in the main reservoir 51 is precluded from rising above the inlet ends 74 of the overflow tubes 70 and thus cannot be carried with the air stream passing out of the humidifier 9 through the air flow cap assembly 15.

The relief float 68 is sized to almost fill the overflow reservoir 56 so that the compressible volume of the humidifier is minimized. The relief float 68 is pivoted at one edge via means illustrated as a pin 78 through the relief float 68 pivotably engaged with spaced hook-like projections 80 from the bottom wall 64, however, many other means of pivotably mounting the float could be used. The outlet opening 53 is located between the center of gravity of the relief float 68 and the means by which it is pivotally mounted so that a force in excess of the weight of the relief float 68 will be applied to seal shut the outlet opening 53. Such sealing is provided by engagement of a resilient rubber disc 82 carried by a recess in the relief float 68 with an annular lip 84 around the outlet opening 53, which seal will preclude escape of air under pressure (e.g., 2 psi above atmospheric pressure) when the humidifier 9 is operating normally. As illustrated, the lips 84 and the outlet opening are formed on a metal (e.g., brass) insert threadably engaged with the bottom wall 64, which like the rest of the walls in the bottom cap assembly 50 is formed of a rigid polymeric material.

The hollow cylindrical structure 72 in which the overflow tubes 70 are formed has spaced axially extending, inwardly projecting ribs 88 which define its inner surface and guide the inlet float 52 while providing minimal contact therewith. The hollow cylindrical structure 72 also has an axially extending through slot 90 which affords a uniform water level across the bottom of the main reservoir 51. A disc-like top wall 92 with a central opening is attached to the upper end of the cylindrical structure 72 to restrict removal of the water inlet float 52 therefrom when the humidifier 9 is disassembled. Thus the hollow cylindrical structure 72 not only provides the overflow tubes 70, but also affords both guiding and stability for the water inlet float 52, while protecting it from damage when the humidifier 9 is disassembled.

The present invention has been described with reference to one embodiment thereof which is particularly adapted so that humidifiers of the type described in U.S. Pat. No. 4,225,542 can be retrofitted by replacing their bottom caps with the bottom cap assembly 50 described herein. It will be appreciated that upon complete redesigns, the improvement according to the present invention could be incorporated in a humidifier in an entirely different form and still provide the desired function of releasing water should an inlet water valve means malfunction. Thus, the scope of the present invention should not be limited to the structure described, but only by the language of the dependent claims and their equivalents.

I claim:

1. In a humidifier for a ventilating system comprising:
    means for defining a main reservoir adapted for containing water;

a water supply tube adapted to be coupled to a source of water under pressure for conducting water to said main reservoir;

inlet float means for allowing flow of water through said supply tube when water in said main reservoir is below a first predetermined level and for normally stopping flow through said supply tube when water in said main reservoir reaches said first predetermined level;

a wick having a bottom end portion projecting into said main reservoir and an opposite end portion projecting from said main reservoir; and means for directing a flow of air under greater than atmospheric pressure over said wick to carry away water evaporated from said wick, the improvement wherein:

said humidifier further includes means for defining an overflow reservoir comprising a housing having an outlet opening communicating between said overflow reservoir and the atmosphere in a bottom portion of said overflow reservoir;

outlet float means for sealing said outlet opening when water in said overflow reservoir is below a second predetermined level and for opening said outlet opening when water in said overflow reservoir rises above said second predetermined level; and an overflow tube having an inlet end within said main reservoir above said first and second predetermined levels and an outlet end in said overflow reservoir;

so that should water in said main reservoir rise above said first predetermined level, it will be conducted by said overflow tube to said overflow reservoir and upon reaching said second predetermined level, will open said outlet float means and escape through said outlet opening to the atmosphere to preclude flooding of said means for directing air.

2. A humidifier according to claim 1 wherein said outlet float means comprises a relief float almost filling said overflow reservoir, said relief float being pivotally mounted at one edge on said housing; and said outlet opening is between said one edge and the center of gravity of said relief float.

3. A humidifier according to claim 1 wherein said inlet float means includes an inlet float, and said humidifier further includes a hollow cylindrical structure projecting upwardly from said main reservoir, having said overflow tube formed therein, having an inner surface shaped to guide the movement of said inlet float, and includes wall means at the ends of said hollow cylindrical structure for retaining said inlet float within said hollow cylindrical structure.

4. In a humidifier for a ventilating system comprising:

means for defining a main reservoir adapted for containing water;

a water supply tube adapted to be coupled to a source of water under pressure for conducting water to said main reservoir;

inlet float means including an inlet float for allowing flow of water through said supply tube when water in said main reservoir is below a first predetermined level and for normally stopping flow through said supply tube when water in said main reservoir reaches said first predetermined level;

a wick having a bottom end portion projecting into said main reservoir and an opposite end portion projecting from said main reservoir; and means for directing a flow of air under greater than atmospheric pressure over said wick to carry away water evaporated from said wick, the improvement wherein said humidifier further includes:

means for defining an overflow reservoir comprising a housing having an outlet opening in a bottom portion of said overflow reservoir;

outlet float means for sealing said outlet opening when water in said overflow reservoir is below a second predetermined level and for opening said outlet opening when water in said overflow reservoir rises above said second predetermined level;

a hollow cylindrical structure projecting upwardly from said main reservoir, having an overflow tube formed therein with an inlet end of said overflow tube within said main reservoir above said first and second predetermined levels and an outlet end of said overflow tube in said overflow reservoir, said cylindrical structure having an inner surface shaped to guide the movement of said inlet float; and wall means at the ends of said hollow cylindrical structure for retaining said inlet float within said hollow cylindrical structure, so that should water in said main reservoir rise above said first predetermined level, it will be conducted by said overflow tube to said overflow reservoir and upon reaching said second predetermined level, will open said outlet float means and escape through said outlet opening to preclude flooding of said means for directing air.

5. A humidifier according to claim 4 wherein said outlet float means comprises a relief float almost filling said overflow reservoir, said relief float being pivotally mounted at one edge on said housing; and said outlet opening is between said one edge and the center of gravity of said relief float.

* * * * *